US010640765B2

(12) United States Patent
Smith et al.

(10) Patent No.: US 10,640,765 B2
(45) Date of Patent: May 5, 2020

(54) METHODS FOR PRODUCING POLYNUCLEOTIDE LIBRARIES IN VACCINIA VIRUS/EUKARYOTIC CELLS

(71) Applicant: Vaccinex, Inc., Rochester, NY (US)

(72) Inventors: Ernest Smith, W. Henrietta, NY (US); Shuying Shi, Rochester, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 16/384,078

(22) Filed: Apr. 15, 2019

(65) Prior Publication Data

US 2019/0241889 A1 Aug. 8, 2019

Related U.S. Application Data

(63) Continuation of application No. 16/320,950, filed as application No. PCT/US2017/044688 on Jul. 31, 2017.

(60) Provisional application No. 62/370,009, filed on Aug. 2, 2016.

(51) Int. Cl.
*C40B 50/06* (2006.01)
*C12N 15/10* (2006.01)

(52) U.S. Cl.
CPC ..... *C12N 15/1082* (2013.01); *C12N 15/1037* (2013.01); *C12N 15/1093* (2013.01); *C40B 50/06* (2013.01)

(58) Field of Classification Search
None
See application file for complete search history.

(56) References Cited

U.S. PATENT DOCUMENTS

| 5,445,953 | A  | 8/1995  | Dorner       |
| 5,770,212 | A  | 6/1998  | Falkner      |
| 6,576,754 | B2 | 6/2003  | Hall         |
| 6,706,477 | B2 | 3/2004  | Zauderer     |
| 6,872,518 | B2 | 3/2005  | Zauderer     |
| 7,700,102 | B2 | 4/2010  | Hall         |
| 7,772,380 | B2 | 8/2010  | Porcelli     |
| 7,858,559 | B2 | 12/2010 | Zauderer     |
| 7,858,599 | B2 | 12/2010 | Hander       |
| 7,919,594 | B2 | 4/2011  | Smith        |
| 8,022,043 | B2 | 9/2011  | Porcelli     |
| 8,067,247 | B2 | 11/2011 | Belin        |
| 8,496,938 | B2 | 7/2013  | Smith        |
| 8,535,687 | B2 | 9/2013  | Draghia-Akli |
| 8,637,026 | B2 | 1/2014  | Zauderer     |
| 8,790,652 | B2 | 7/2014  | Basile       |
| 8,816,058 | B2 | 8/2014  | Smith        |
| 8,834,883 | B2 | 9/2014  | Croy         |
| 9,090,709 | B2 | 7/2015  | Fisher       |
| 9,139,809 | B2 | 9/2015  | Porcelli     |
| 9,243,068 | B2 | 1/2016  | Evans        |
| 9,249,227 | B2 | 2/2016  | Smith        |
| 9,371,352 | B2 | 6/2016  | Porcelli     |
| 9,382,327 | B2 | 7/2016  | Smith        |
| 9,447,191 | B2 | 9/2016  | Takayanagi   |
| 9,512,224 | B2 | 12/2016 | Zauderer     |
| 9,598,495 | B2 | 3/2017  | Smith        |
| 9,603,922 | B2 | 3/2017  | Donda        |
| 9,605,055 | B2 | 3/2017  | Smith        |
| 9,676,840 | B2 | 6/2017  | Smith        |
| 9,701,958 | B2 | 7/2017  | Smith        |
| 9,708,601 | B2 | 7/2017  | Smith        |
| 9,790,271 | B2 | 10/2017 | Zauderer     |
| 9,809,654 | B2 | 11/2017 | Bruno        |
| 9,828,435 | B2 | 11/2017 | Evans        |
| 9,890,213 | B2 | 2/2018  | Smith        |
| 9,963,504 | B2 | 5/2018  | Klimatcheva  |
| 10,111,950 | B2 | 10/2018 | Porcelli    |
| 10,301,393 | B2 | 5/2019  | Smith       |
| 2003/0022157 | A1 | 1/2003 | Zauderer   |
| 2005/0266425 | A1 | 12/2005 | Zauderer  |
| 2009/0304627 | A1 | 12/2009 | Draghia-Akli |
| 2010/0081575 | A1 | 4/2010 | Williamson  |
| 2011/0008322 | A1 | 1/2011 | Zauderer    |
| 2013/0095118 | A1 | 4/2013 | Smith       |
| 2013/0164325 | A1 | 6/2013 | Porcelli    |
| 2013/0288927 | A1 | 10/2013 | Smith      |
| 2013/0302320 | A1 | 11/2013 | Smith      |
| 2014/0303358 | A1 | 10/2014 | Takayanagi |
| 2016/0152971 | A1 | 6/2016 | Smith       |
| 2019/0112388 | A1 | 4/2019 | Smith       |

FOREIGN PATENT DOCUMENTS

| EP | 1516932       | 3/2005 |
| WO | 00028016 A1   | 5/2000 |
| WO | 20020062822   | 8/2002 |
| WO | 2004029206    | 4/2004 |
| WO | 2005055936    | 6/2005 |

(Continued)

OTHER PUBLICATIONS

Boesen, Non-Final Office Action issued in U.S. Appl. No. 13/844,388 dated Apr. 29, 2016, 8 pages.
Carroll, M. et al., (1997), "Host Range and Cytopathogenicity of the Highly Attenuated MVA Strain of Vaccinia Virus: Propagation and Generation of Recombinant Viruses in a Nonhuman Mammalian Cell Line", Virology, 238: 198-211.
Chakrabarti et al., "Compact, Synthetic, Vaccinia Virus Early/Late Promoter for Protein Expression", BioTechniques, 1997, pp. 1094-1097, vol. 23 No. 6, Informa Healthcare USA, Inc., England.
Chou et al, "An Overview of the Vaccinia Virus Infectome: A Survey of the Proteins of the Poxvirus-Infected Cell", Journal of Virology, Feb. 2012, pp. 1487-1499, vol. 86, No. 3.

(Continued)

*Primary Examiner* — Christian C Boesen

(57) ABSTRACT

This disclosure provides an improved method of constructing a library of polynucleotides of interest in a poxvirus, e.g., vaccinia virus vector system, where the polynucleotides of interest encode polypeptides of interest. The method comprises constructing the library in the presence of an inhibitor of poxvirus assembly, e.g., rifampicin, which allows construction of libraries with higher complexity and diversity than previous methods.

30 Claims, No Drawings

Specification includes a Sequence Listing.

(56) References Cited

FOREIGN PATENT DOCUMENTS

| WO | 2011110621 | 9/2011 |
|---|---|---|
| WO | 2011110642 | 9/2011 |
| WO | 2011140249 | 11/2011 |
| WO | 2013163602 | 10/2013 |
| WO | 2017184951 | 10/2017 |
| WO | 2018026715 | 2/2018 |
| WO | 2018156509 | 8/2018 |
| WO | 2018175179 | 9/2018 |
| WO | 2018204895 | 11/2018 |

OTHER PUBLICATIONS

Chung et al., "Vaccinia Virus Proteome: Identification of Proteins in Vaccinia Virus Intracellular Mature Virion Particles", Journal of Virology, Mar. 2006, pp. 2127-2140, vol. 80, No. 5.

Colbére-Garapin, F., et al., (1981), "A new dominant hybrid selective marker for higher eukaryotic cells", Journal of Molecular Biology, vol. 150(1): 1-14.

Dehaven et al., "The Vaccinia Virus A56 Protein: A Multifunctional Transmembrane Glycoprotein that Anchors Two Secreted Viral Proteins", Journal of General Virology, 2011, pp. 1971-1980, vol. 92.

Deng, L., et al., (2007), "Indentification of Novel Antipoxiral Agents: Mitoxantron Inhibits Vaccinia Virus Replication by Blocking Virion Assembly", Journal of Virology, vol. 81(24), pp. 13392-13402.

Earl, P., L., et al., (1990), "Removal of Cryptic Poxvirus Transcription Termination Signals from Human Immunodeficiency Virus Type 1 Envelope Gene Enhances Expression and Immunogenicity of a Recombinant Vaccinia Virus", Journal of Virology, vol. 64(5), 2448-2451.

Fenner, F. (1959), "Genetic studies with mammalian poxviruses: II. Recombination between two strains of vaccinia virus in single HeLa cells", Virology, vol. 8: 499-507.

Fenner, F., et al., (1958), "Genetic studies with mammalian poxviruses: I. Demonstration of recombination between two strains of vaccinia virus", Virology, vol. 5: 530-548.

Furuyama et al., "Identification of a Novel Transmembrane Semaphorin Expressed on Lymphocytes", Journal of Biological Chemistry, Dec. 27, 1996, pp. 33376-33381, vol. 271 No. 52.

Galmiche et al., "Expression of a Functional Single Chain Antibody on the Surface of Extracellular Enveloped Vaccinia Virus as a Step Towards Selective Tumour Cell Targeting", Journal of General Virology, 1997, pp. 3019-3027, vol. 78, Great Britain.

GenBank Accession No. Q01218 retrieved from http://ibis.internal.epo.org/exam/dbfetch.jsp?id=UNIPROT:Q01218 on Apr. 1, 1993.

Hammond et al., "A Synthetic Vaccinia Virus Promoter with Enhanced Early and Late Activity", Journal of Virological Methods, 1997, pp. 135-138, vol. 66 No. 1, Journal of Virological Methods.

Hebert et al., "The Molecular Dating Game: An Antibody Heavy Chain Hangs Loose with a Chaperone while Waiting for Its Life Partner", Molecular Cell, 2009, pp. 635-636, vol. 34 No. 6, Cell Press, United States.

Ho et al., "Display and Selection of scFv antibodies on HEK-293T Cells", Methods of Molecular Biology, 2009, pp. 99-113, vol. 562.

International Preliminary Report on Patentability (Chapter I) for PCT/US2013/038497 dated Oct. 28, 2014.

International Search Report and Written Opinion dated Oct. 6, 2017 issued in PCT/US2017/044688.

International Search Report and Written Opinion for PCT/US2013/038497 dated Sep. 6, 2013.

Kotwal G., et al., (1988), "Analysis of a large cluster of nonessential genes deleted from a vaccinia virus terminal transposition mutant", Virology, vol. 167: 524-537.

Lorenzo et al., "Intracellular Localization of Vaccinia Virus Extracellular Enveloped Virus Envelope Proteins Individually Expressed Using a Semliki Forest Virus Replicon", Journal of Virology, 2000, pp. 10535-10550, vol. 74 No. 22, American Society for Microbiology, United States.

Mayr, A., et al., (1975), "Abstammung, Eigenschaften and Verwendung des attenuierten Vaccinia-Stammes MVA", vol. 3(1), pp. 6-14— Available in German Only.

Merchlinsky, M., et al., (1997), "Construction and Characterization of Vaccinia Direct Ligation Vectors", Virology, 238: 444-451.

Moss, B., (1991), "Vaccinia virus: a tool for research and vaccine development", Science, vol. 252(5013), pp. 1662-1667.

Moss, B., et al., (1969), "Rifampicin: a Specific Inhibitor of Vaccinia Virus Assembly", Nature, vol. 224, pp. 1280-1284.

Mulligan, R. C. et al., (1981), "Selection for animal cells that express the *Escherichia coli* gene coding for xanthine-guanine phosphoribosyltransferase", Proc. Natl. Acad. Sci. USA vol. 78(4): 2072-2076.

O'Hare, K.., et al., (1981), "Transformation of mouse fibroblasts to methotrexate resistance by a recombinant plasmid expressing a prokaryotic dihydrofolate reductase", Proc. Natl. Acad. Sci. USA, vol. 78(3): 1527-1531.

Office Action for U.S. Appl. No. 13/844,388 dated Jan. 13, 2015.

Office Action for U.S. Appl. No. 13/844,388 dated Sep. 25, 2015.

Perkus, M., et al., (1986), "Insertion and deletion mutants of vaccinia virus", Virology, vol. 152(2): 285-297.

Roberts et al., "Vaccinia Virus Morphogenesis and Dissemination", Trends in Microbiology, 2008, pp. 472-479, vol. 16 No. 10, Elsevier Trends Journals, England.

Santerre, R., et al., (1984), "Expression of prokaryotic genes for hygromycin B and G418 resistance as dominant-selection markers in mouse L cells", Gene, vol. 30: 147-156.

Scheiflinger, F., et al., (1992), "Construction of chimeric vaccinia viruses by molecular cloning and packaging",Proc. Natl. Acad. Sci. USA, Biochemistry, vol. 89, pp. 9977-9981.

Smith et al., "Nucleotide Sequence of 42 kbp of Vaccinia Virus Strain WR From Near the Right Inverted Terminal Repeat", Journal of General Virology, 1991, pp. 1349-1376, vol. 72, Great Britain.

Smith et al., "The Formation and Function of Extracellular Enveloped Vaccinia Virus", Journal of General Virology, 2002, pp. 2915-2931, vol. 83 Pt. 12, Society for General Microbiology, England.

Smith, E., et al., (2001), "Lethality-Based Selection of Recombinant Genes in Mammalian Cells: Application to Identifying Tumor Antigens" Nature Medicine, 7(8): 967-972.

Sodeik, B., et al., (1994), "Assembly of Vaccinia Virus: Effects of Rifampin on the Intracellular Distribution of Viral Protein p65", Journal of Virology, vol. 68(2), pp. 1103-1114.

Sutter, G., et al., (1992), "Nonreplicating vaccinia vector efficiently expresses recombinant genes", Proc. Natl. Acad. Sci. USA, vol. 89: 10847-10851.

Syzbalska, E., et al., (1962), "Genetics of Human Cell Lines, IV. DNA-Mediated Heritable Transformation of a Biochemical Trait", Proc. Natl. Acad. Sci. USA, vol. 48: 2026-2034.

USPTO, Applicant-1nititated Interview Summary issued in U.S. Appl. No. 14/977,067, dated Mar. 10, 2017, 3 pages.

USPTO, Final Office Action for U.S. Appl. No. 13/844,388 dated Feb. 9, 2017, 7 pages.

USPTO, Notice of Allowance issued in U.S. Appl. No. 14/977,067, dated Mar. 14, 2017, 10 pages.

Wigler M., et al., (1980), "Transformation of mammalian cells with an amplifiable dominant-acting gene", Proc. Natl. Acad. Sci. USA, vol. 77(6): 3567-3570.

Wigler, M. et al., (1977), "Transfer of purified herpes virus thymidine kinase gene to cultured mouse cells", Cell, vol. 11(1): 223-232.

METHODS FOR PRODUCING POLYNUCLEOTIDE LIBRARIES IN VACCINIA VIRUS/EUKARYOTIC CELLS

CROSS-REFERENCE TO RELATED APPLICATIONS

This application is a continuation of U.S. patent application Ser. No. 16/320,950, filed Jan. 25, 2019, which is a U.S. National Stage Entry of PCT Application PCT/US2017/044688, filed Jul. 31, 2017, which claims the benefit of U.S. Provisional Patent Application Ser. No. 62/370,009, filed Aug. 2, 2016, which are each hereby incorporated by reference in their entireties.

REFERENCE TO SEQUENCE LISTING SUBMITTED ELECTRONICALLY

The content of the electronically submitted sequence listing in ASCII text file (Name "Sequence-Listing.txt; Size: 4,096 bytes; and Date of Creation: Jan. 24, 2019") filed with the application is incorporated herein by reference in its entirety.

BACKGROUND

This disclosure relates to an improved method of identifying proteins of interest, e.g., binding molecules such as antibodies or fragments thereof, in eukaryotic cells, and in particular, improved method of producing protein libraries, e.g., antibody heavy and/or light chain libraries for expression in eukaryotic cells.

Eukaryotic Expression Libraries

A basic tool in the field of molecular biology is the conversion of poly $(A)^+$ mRNA to double-stranded (ds) cDNA, which then can be inserted into a cloning vector and expressed in an appropriate host cell. A method common to many cDNA cloning strategies involves the construction of a "cDNA library" which is a collection of cDNA clones derived from the poly$(A)^+$ mRNA derived from a cell of the organism of interest. For example, in order to isolate cDNAs which express immunoglobulin or antibody subunit polypeptides, a cDNA library might be prepared from pre-B cells, B cells, or plasma cells. Methods of constructing cDNA libraries in different expression vectors, including filamentous bacteriophage, bacteriophage lambda, cosmids, and plasmid vectors, are known.

Many different methods of isolating target genes from cDNA libraries have been utilized, with varying success. These include, for example, the use of nucleic acid hybridization probes, which are labeled nucleic acid fragments having sequences complementary to the DNA sequence of the target gene. When this method is applied to cDNA clones in transformed bacterial hosts, colonies or plaques hybridizing strongly to the probe are likely to contain the target DNA sequences. Hybridization methods, however, do not require, and do not measure, whether a particular cDNA clone is expressed. Alternative screening methods rely on expression in the bacterial host, for example, colonies or plaques can be screened by immunoassay for binding to antibodies raised against the protein of interest. Assays for expression in bacterial hosts are often impeded, however, because, e.g., the protein is not sufficiently expressed in bacterial hosts, the protein is expressed in the wrong conformation, or the protein is not processed, and/or transported as it would in a eukaryotic system. Many of these problems have been encountered in attempts to produce antibody molecules in bacterial hosts, as alluded to above.

Accordingly, use of eukaryotic, e.g., yeast or mammalian expression libraries to isolate cDNAs encoding proteins of interest, e.g., binding molecules such as antibodies or antigen-binding fragments thereof, offer several advantages over bacterial libraries. For example, binding molecules such as antibodies or antigen-binding fragments thereof, and subunits thereof, expressed in eukaryotic hosts can be functional and can undergo typical eukaryotic posttranslational modification. A protein ordinarily transported through the intracellular membrane system to the cell surface can complete the transport process. Further, use of a eukaryotic system makes it possible to isolate polynucleotides encoding proteins of interest based on functional expression of eukaryotic RNA or protein. For example, binding molecules such as antibodies or antigen-binding fragments thereof can be isolated based on their specificity for a given antigen. See, e.g., U.S. Pat. No. 7,858,559, U.S. Patent Appl. Publ. No. 2016-0152971, and U.S. Prov. Appl. No. 62/326,501, filed on Apr. 22, 2016, each of which is incorporated herein by reference in its entirety. See also Smith et al., *Nature Medicine* 7:967-972 (2001).

Poxvirus Vectors

Poxvirus vectors are used extensively as expression vehicles for protein and antigen expression in eukaryotic cells. The ease of cloning and propagating vaccinia in a variety of host cells has led to the widespread use of poxvirus vectors for expression of foreign protein and as vaccine delivery vehicles (Moss, B., *Science* 252:1662-7 (1991)).

Traditionally, poxvirus vectors were not used to identify unknown genes of interest from a complex population of clones, because a high efficiency, high titer-producing method of cloning did not exist for pox viruses. The present inventors, however, developed a method for generating diverse cDNA libraries in recombinant poxviruses using tri-molecular recombination. See, e.g., Zauderer, U.S. Pat. No. 6,706,477, issued Mar. 16, 2004, and Zauderer et al., U.S. Pat. No. 7,858,559, issued Dec. 28, 2010, each of which is incorporated herein by reference in its entirety.

Tri-molecular recombination by itself is a high efficiency, high titer-producing method for producing recombinant poxviruses. There remains a need to further enhance the process of using tri-molecular recombination to yield an even greater amount of recombinant viruses.

SUMMARY

This disclosure provides a method of constructing a library that includes a plurality of polynucleotides of interest. The method includes: (a) cleaving an isolated poxvirus genome to produce a first viral fragment and a second viral fragment, where the first fragment is nonhomologous with the second fragment; (b) providing a population of transfer plasmids each including a polynucleotide of interest flanked by a 5' flanking region and a 3' flanking region, where the 5' flanking region includes a region homologous to the 3' end of the first viral fragment and the 3' flanking region includes a region homologous to the 5' end of the second viral fragment; and where the transfer plasmids are capable of homologous recombination with the first and second viral fragments such that a viable poxvirus genome is formed; (c) introducing the transfer plasmids and the first and second viral fragments into a mammalian host cell permissive for poxvirus infectivity; (d) adding an inhibitor of poxvirus assembly; and (e) allowing the transfer plasmid and the first and second viral fragments to undergo homologous recombination, thereby producing a library of viable modified poxvirus genomes each including a heterologous nucleic acid. In certain aspects the method can further include (f) recovering the library. In certain aspects, step (c) can include transfecting the mammalian host cell with the transfer plasmids and the first and second viral fragments, where the host cell is maintained in cell culture medium following transfection.

In certain aspects, the inhibitor of poxvirus assembly can be rifampicin (rifampin) or a derivative thereof. In certain aspects, the rifampicin or derivative thereof can be added to the cell culture medium that includes the transfected cells at about 6 hours, about 12 hours, about 18 hours, about 24 hours, about 30 hours, about 36 hours, about 42 hours, about 48 hours, about 54 hours, or about 60 hours following transfection. In certain aspects, the rifampicin or derivative thereof is added to the cell culture medium at a concentration of about 30 µg/ml, about 40 µg/ml, about 50 µg/ml, about 60 µg/ml, about 70 µg/ml, about 80 µg/ml, about 90 µg/ml, about 100 µg/ml, about 110 µg/ml, about 120 µg/ml, or about 130 µg/ml. In certain aspects, the rifampicin or derivative thereof is allowed to remain cell culture medium for about one day, about two days, about three days, about four days or about five days. In certain aspects, the cell culture medium is changed following treatment with rifampicin or a derivative thereof, and the transfected host cells can be further cultured without rifampicin for about one day, about two days, or about three days.

The method as provided herein can result in an increased number of independent modified poxvirus genomes than a library constructed by the method, but in the absence of the inhibitor of poxvirus assembly. In certain aspects, the number of independent modified poxvirus genomes is increased by at least about one-fold, about five-fold, about ten-fold, about fifteen-fold, about twenty-fold, about twenty-five-fold, or about thirty-fold as compared to a library constructed by the method, but in the absence of the inhibitor of poxvirus assembly. In certain aspects, the library can include an increased virus titer relative to a library constructed by the method, but in the absence of the inhibitor of poxvirus assembly.

In certain aspects of the method as provided herein, the isolated poxvirus genome can include a first recognition site for a first restriction endonuclease and a second recognition site for a second restriction endonuclease. According to this aspect, the first and second viral fragments can be produced by digesting the viral genome with the first restriction endonuclease and the second restriction endonuclease, and then isolating the first and second viral fragments. In certain aspects, the isolated poxvirus genome is an isolated vaccinia virus genome. In certain aspects, the isolated vaccinia virus genome can be a WR genome or a modified derivative thereof, or a Modified Vaccinia virus Ankara (MVA) genome or a modified derivative thereof. In certain aspects, the first and second restriction enzyme recognition sites can be situated in a vaccinia virus HindIII J fragment. In certain aspects, the first restriction enzyme can be Not I. In certain aspects, the second restriction enzyme site can be Apa I. In certain aspects, the isolated vaccinia virus genome can be a v7.5/tk virus genome or a vEL/tk virus genome. In certain aspects, the helper virus can be a fowlpox virus. In certain aspects, the 5' and 3' flanking regions of the transfer plasmid are capable of homologous recombination with a vaccinia virus thymidine kinase gene. In certain aspects, the 5' and 3' flanking regions of the transfer plasmid are capable of homologous recombination with a vaccinia virus HindIII J fragment.

In certain aspects of the method provided herein, each transfer plasmid can include an insert polynucleotide of interest ligated into a plasmid such as, but not limited to: pVHE, pVLE, and/or pVKE. In certain aspects, each polynucleotide of interest can include a coding region of a polypeptide of interest capable of expression in a vaccinia virus-infected cell. In certain aspects, each polynucleotide of interest can encode an antibody or an antibody subunit polypeptide including an antibody heavy chain variable region or antigen-binding fragment thereof, an antibody light chain variable region or antigen-binding fragment thereof, or a combination thereof. In certain aspects, each antibody subunit polypeptide can further include a constant region or fragment thereof, a signal peptide capable of directing cell surface expression or secretion of the antibody subunit polypeptide, or a combination thereof. In certain aspects each transfer plasmid can further include a transcriptional control region in operable association with the polynucleotide of interest, where the transcriptional control region functions in the cytoplasm of a vaccinia virus-infected cell. In certain aspects the transcriptional control region can include a poxvirus promoter, e.g., a vaccinia p7.5 promoter, a vaccinia pEL promoter, or a vaccinia MH-5 promoter.

In certain aspects of the method as provided herein, the host cell is capable of packaging the modified vaccinia virus genomes into infectious vaccinia virus particles. According to this aspect, the transfer plasmids and the first and second viral fragments can be introduced into a mammalian host cell that includes, or has been infected to include, a helper virus, where the host cell is non-permissive for the production of infectious virus particles of the helper virus, but supports packaging the modified vaccinia virus genomes into infectious vaccinia virus particles.

DETAILED DESCRIPTION

This disclosure provides a method of producing a library of polynucleotides encoding functional polypeptides of interest, e.g., binding molecules such as antibodies or antigen-binding fragments thereof, or subunits thereof, in a eukaryotic system, where the library includes improved complexity and diversity over existing methods. For example, the disclosure provides a method of constructing an expression library of polynucleotides which encode and can express polypeptides of interest, e.g., binding molecules such as antibodies or antigen-binding fragments thereof, or subunits thereof, where polynucleotides encoding polypeptides of interest can be identified and isolated from the expression library, where the library is constructed in a poxvirus, e.g., vaccinia virus vector, where library screening takes place in eukaryotic, e.g., mammalian host cells, and where the method provides a library of increased complexity and diversity over existing methods.

The disclosure provides for the construction of complex polynucleotide libraries in eukaryotic host cells using poxvirus e.g., vaccinia virus vectors constructed by tri-molecular recombination. The complexity and diversity of the library can be improved by contacting the mammalian host cells in which the library is constructed with an inhibitor of poxvirus, e.g., vaccinia virus replication, e.g., rifampicin (rifampin) for a period of time during the construction process.

Definitions

The term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative or judicial body to be, "naturally-occurring."

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, and derivatization by known protecting/ blocking groups, proteolytic cleavage, or modification by non-naturally occurring amino acids. A polypeptide can be derived from a biological source or produced by recombinant technology, but is not necessarily translated from a designated nucleic acid sequence. It can be generated in any manner, including by chemical synthesis.

A polypeptide as disclosed herein can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid, e.g., a serine or an asparagine.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides that have been separated, fractionated, or partially or substantially purified by any suitable technique.

As used herein, the term "non-naturally occurring" polypeptide, or any grammatical variants thereof, is a conditional term that explicitly excludes, but only excludes, those forms of the polypeptide that are well-understood by persons of ordinary skill in the art as being "naturally-occurring," or that are, or might be at any time, determined or interpreted by a judge or an administrative or judicial body to be, "naturally-occurring."

Other polypeptides disclosed herein are fragments, derivatives, analogs, or variants of the foregoing polypeptides, and any combination thereof. The terms "fragment," "variant," "derivative" and "analog" as disclosed herein include any polypeptides that retain at least some of the properties of the corresponding native antibody or polypeptide, for example, specifically binding to an antigen. Fragments of polypeptides include, for example, proteolytic fragments, as well as deletion fragments, in addition to specific antibody fragments discussed elsewhere herein. Variants of, e.g., a polypeptide include fragments as described above, and also polypeptides with altered amino acid sequences due to amino acid substitutions, deletions, or insertions. In certain aspects, variants can be non-naturally occurring. Non-naturally occurring variants can be produced using art-known mutagenesis techniques. Variant polypeptides can include conservative or non-conservative amino acid substitutions, deletions or additions. Derivatives are polypeptides that have been altered so as to exhibit additional features not found on the original polypeptide. Examples include fusion proteins. Variant polypeptides can also be referred to herein as "polypeptide analogs." As used herein a "derivative" of a polypeptide can also refer to a subject polypeptide having one or more amino acids chemically derivatized by reaction of a functional side group. Also included as "derivatives" are those peptides that contain one or more derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence, to the antigen to which the binding molecule, e.g., immunoglobulin or antibody, binds. Methods of identifying nucleotide and amino acid conservative substitutions that do not eliminate antigen binding are well-known in the art (see, e.g., Brummell et al., *Biochem.* 32:1180-1 187 (1993); Kobayashi et al., *Protein Eng.* 12(10):879-884 (1999); and Burks et al., *Proc. Natl. Acad. Sci. USA* 94: 412-417 (1997)).

The term "polynucleotide" is intended to encompass a singular nucleic acid as well as plural nucleic acids, and refers to an isolated nucleic acid molecule or construct, e.g., messenger RNA (mRNA), cDNA, or plasmid DNA (pDNA). A polynucleotide can include a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, that has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

As used herein, a "non-naturally occurring" polynucleotide, or any grammatical variants thereof, is a conditional definition that explicitly excludes, but only excludes, those forms of the polynucleotide that are well-understood by persons of ordinary skill in the art as being "naturally-occurring," or that are, or that might be at any time, determined or interpreted by a judge or an administrative or judicial body to be, "naturally-occurring."

As used herein, a "coding region" is a portion of nucleic acid that consists of codons translated into amino acids.

Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding region. Two or more coding regions can be present in a single polynucleotide construct, e.g., on a single vector, or in separate polynucleotide constructs, e.g., on separate (different) vectors. Furthermore, any vector can contain a single coding region, or can include two or more coding regions, e.g., a single vector can separately encode an antibody heavy chain variable region and an antibody light chain variable region. In addition, a vector, polynucleotide, or nucleic acid can include heterologous coding regions, either fused or unfused to another coding region. Heterologous coding regions include without limitation, those encoding specialized elements or motifs, such as a secretory signal peptide or a heterologous functional domain.

In certain embodiments, the polynucleotide or nucleic acid is DNA. In the case of DNA, a polynucleotide including a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA in predetermined cells. Other transcription control elements, besides a promoter, for example enhancers, operators, repressors, and transcription termination signals, can be operably associated with the polynucleotide to direct cell-specific transcription.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins). In certain aspects the transcription control regions can be poxvirus, e.g., vaccinia virus transcription control regions, discussed in more detail elsewhere herein.

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide can be RNA, for example, in the form of messenger RNA (mRNA), transfer RNA, or ribosomal RNA.

Polynucleotide and nucleic acid coding regions can be associated with additional coding regions that encode secretory or signal peptides, which direct the secretion of a polypeptide encoded by a polynucleotide as disclosed herein. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells can have a signal peptide fused to the N-terminus of the polypeptide, which is cleaved from the complete or "full length" polypeptide to produce a secreted or "mature" form of the polypeptide. In certain embodiments, the native signal peptide, e.g., an antibody heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, can be used. For example, the wild-type leader sequence can be substituted with the leader sequence of human tissue plasminogen activator (TPA) or mouse ß-glucuronidase.

As used herein, two polynucleotide regions are considered to be "homologous" if they can undergo homologous recombination in a host cell, e.g., a eukaryotic or mammalian host cell. Homologous recombination is a type of genetic recombination in which nucleotide sequences are exchanged between two similar or identical molecules of DNA. In general, homologous recombination can occur when two single polynucleotide strands, e.g., overhanging ends of double stranded DNA, can anneal to each other due to complementary base pairing. The strands need not be 100% complementary; moreover, the single stranded regions need not be particularly long. The many mechanisms and functions of homologous recombination are well understood by those of ordinary skill in the field of molecular biology.

As used herein, a "library" is a representative genus of polynucleotides, e.g., a group of polynucleotides related through, for example, their origin from a single animal species, tissue type, organ, or cell type, where the library collectively includes at least two different species within a given genus of polynucleotides. A library of polynucleotides can include, e.g., at least two, at least 5, at least 10, 100, $10^3$, $10^4$, $10^5$, $10^6$, $10^7$, $10^8$, or $10^9$ different species within a given genus of polynucleotides. In certain aspects, a library of polynucleotides as provided herein can encode a plurality of polypeptides that contains a polypeptide of interest. In certain aspects, a library of polynucleotides as provided herein can encode a plurality of antibody subunit polypeptides, e.g., heavy chain subunit polypeptides or light chain subunit polypeptides. In this context, a "library" as provided herein includes polynucleotides of a common genus, the genus being polynucleotides encoding antibody subunit polypeptides of a certain type and class e.g., a library might encode a human μ, γ-1, γ-2, γ-3, γ-4, α-1, α-2, ε, or δ heavy chain, or a human κ or λ light chain. Although each member of any one library constructed according to the methods provided herein can encode the same heavy or light chain constant region and/or a membrane anchoring domain, the library can collectively include at least two, at least 5, or at least 10, 100, $10^3$, $10^4$, $10^5$, $10^6$, $10^7$, $10^8$, or $10^9$ different variable region associated with the common constant region.

A library as provided herein is constructed in a poxvirus, e.g., a vaccinia virus vector, and thus includes a plurality of modified poxvirus genomes, each containing a heterologous polynucleotide encoding a polypeptide of interest. The "complexity" or "diversity" of a library as provided herein refers to number of different independent modified poxvirus genomes contained within the library. Thus, a library of modified poxvirus genomes can be said to have greater complexity than another library having the same number of total poxvirus genomes where the more complex library contains a greater number of independent modified poxvirus genomes per total poxvirus genomes.

In certain aspects, the library can encode a plurality of antibody single-chain fragments that each include a variable region, such as a light chain variable region or a heavy chain variable region, and/or both a light chain variable region and a heavy chain variable region, e.g., an ScFv fragment.

The disclosure provides methods to construct libraries of polynucleotides encoding polypeptides of interest, e.g., polypeptides comprising antibody subunits or fragment thereof. In addition, the disclosure provides libraries of polypeptides of interest, e.g., polypeptides comprising antibody subunits or fragments thereof constructed in vaccinia virus expression vectors according to the methods described herein.

By "recipient cell" or "host cell" or "cell" is meant a cell or population of cells in which polynucleotide libraries as provided herein can be constructed and/or propagated. A host cell as provided herein is typically a eukaryotic cell or cell line, e.g., a vertebrate, mammalian, rodent, mouse, primate, or human cell or cell line. By "a population of host cells" is meant a group of cultured cells which a "library" as provided herein can be constructed, propagated, and/or expressed. Any host cell which is permissive for vaccinia virus infectivity is suitable for the methods provided by this disclosure. Host cells for use in the methods provided herein can be adherent, e.g., host cells that grow attached to a solid substrate, or, alternatively, the host cells can be in suspension.

Host cells as provided herein can include a constitutive secretory pathway, where proteins, e.g., proteins of interest expressed by a library constructed by the methods provided herein, e.g., a library of polypeptides including antibody subunit polypeptides are secreted from the interior of the cell either to be expressed on the cell membrane surface or to be fully secreted as soluble polypeptides. In certain aspects, proteins of interest expressed on the cell membrane surface are expressed on the surface of an enveloped virus produced by the host cell, e.g., an extracellular enveloped vaccinia virus, or EEV. Membrane-bound forms of antibody subunit polypeptides initially follow the same pathway as fully secreted forms, passing through to the ER lumen, except that they are retained in the ER membrane by the presence of one or more stop-transfer signals, or "transmembrane domains." Transmembrane domains are hydrophobic stretches of about 20 amino acids that adopt an alpha-helical conformation as they transverse the membrane. Membrane embedded proteins are anchored in the phospholipid bilayer of the plasma membrane. Transmembrane forms of polypeptides of interest, e.g., membrane-anchored antibody heavy chain polypeptides typically utilize amino terminal signal peptides as do fully secreted forms.

Signal peptides, transmembrane domains, and cytosolic domains are known for a wide variety of membrane bound and/or fully secreted proteins.

Suitable transmembrane domains can include, but are not limited to the vaccinia virus EEV-specific HA protein A56R, or the EEV-specific vaccinia virus transmembrane proteins A33R, A34R, A36R, or B5R. See, e.g., U.S. Patent Application Publication No. 2013/0288927, published Oct. 31, 2013. In certain aspects the EEV specific protein can be anchored to the viral envelope via palmitoylation, e.g., the vaccinia virus protein F13L. See, e.g., U.S. Provisional Application 62/326,501, filed on Apr. 22, 2016, which is incorporated herein by reference in its entirety.

As used herein, the term "binding molecule" refers in its broadest sense to a molecule that specifically binds to a receptor, e.g., an epitope or an antigenic determinant. As described further herein, a binding molecule can include one or more "antigen binding domains" described herein. A non-limiting example of a binding molecule is an antibody or antigen-binding fragment thereof that retains antigen-specific binding.

The terms "binding domain" and "antigen binding domain" are used interchangeably herein and refer to a region of a binding molecule that is necessary and sufficient to specifically bind to an epitope. For example, an "Fv," e.g., a variable heavy chain and variable light chain of an antibody, either as two separate polypeptide subunits or as a single chain, is considered to be a "binding domain."

Other antigen binding domains include, without limitation, the variable heavy chain (VHH) of an antibody derived from a camelid species (See, e.g., Hamers-Casterman et al., *Nature* 363:446-448 (1993)), or six antibody complementarity determining regions (CDRs) expressed in a fibronectin scaffold. A "binding molecule" as described herein can include one, two, three, four, five, six, seven, eight, nine, ten, eleven, twelve or more "antigen binding domains."

The terms "antibody" and "immunoglobulin" can be used interchangeably herein. An antibody (or a fragment, variant, or derivative thereof as disclosed herein) includes at least the variable region of a heavy chain (for camelid species) or at least the variable regions of a heavy chain and a light chain. Basic antibody structures in vertebrate systems are relatively well understood. See, e.g., Harlow et al., Antibodies: A Laboratory Manual, (Cold Spring Harbor Laboratory Press, 2nd ed. 1988). Unless otherwise stated, the term "antibody" encompasses anything ranging from a small antigen binding fragment of an antibody to a full sized antibody, e.g., an IgG antibody that includes two complete heavy chains and two complete light chains, an IgA antibody that includes four complete heavy chains and four complete light chains and can include a J-chain and/or a secretory component, or an IgM antibody that includes ten or twelve complete heavy chains and ten or twelve complete light chains and can include a J-chain.

The terms "immunoglobulin" and "antibody" include various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\varepsilon$) with some subclasses among them (e.g., $\gamma1$-$\gamma4$ or $\alpha1$-$\alpha2$)). It is the nature of this chain that determines the "class" of the antibody as IgG, IgM, IgA IgG, or IgE, respectively. The antibody subclasses (isotypes) e.g., $IgG_1$, $IgG_2$, $IgG_3$, $IgG_4$, $IgA_1$, $IgA_2$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the antibodies are generated either by hybridomas, B cells or genetically engineered host cells. In the heavy chain, the amino acid sequences run from an N-terminus at the forked ends of the Y configuration to the C-terminus at the bottom of each chain. The basic structure of certain antibodies, e.g., IgG antibodies, includes two heavy chain subunits and two light chain subunits covalently connected via disulfide bonds to form a "Y" structure, also referred to herein as an "H2L2" structure.

The term "epitope" includes any molecular determinant capable of specific binding to an antibody. In certain aspects, an epitope can include chemically active surface groupings of molecules such as amino acids, sugar side chains, phosphoryl, or sulfonyl, and, in certain aspects, can have three dimensional structural characteristics, and or specific charge characteristics. An epitope is a region of a target that is bound by an antibody.

"Multispecific binding molecules or antibodies" or "bispecific binding molecules or antibodies" refer to binding molecules, antibodies, or antigen binding fragments thereof that have the ability to specifically bind to two or more different epitopes on the same or different target(s). "Monospecific" refers to the ability to bind only one epitope.

The term "target" is used in the broadest sense to include substances that can be bound by a binding molecule. A target can be, e.g., a polypeptide, a nucleic acid, a carbohydrate, a lipid, or other molecule. Moreover, a "target" can, for example, be a cell, an organ, or an organism that includes an epitope bound that can be bound by a binding molecule.

Both the light and heavy chains are divided into regions of structural and functional homology. The terms "constant" and "variable" are used functionally. In this regard, it will be appreciated that the variable regions (which can be called "variable domains" interchangeably herein) of both the variable light (VL) and variable heavy (VH) chain portions determine antigen recognition and specificity. Conversely, the constant domains of the light chain (CL) and the heavy chain (e.g., CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains are at the carboxy-terminus of the heavy and light chain, respectively.

The six "complementarity determining regions" or "CDRs" present in a typical antibody antigen binding domain are short, non-contiguous sequences of amino acids that are specifically positioned to form the antigen binding domain as the antibody assumes its three dimensional configuration in an aqueous environment. The remainder of the amino acids in the antigen binding domain, referred to as "framework" regions, show less inter-molecular variability. The framework regions largely adopt a n-sheet conformation and the CDRs form loops that connect, and in some cases form part of, the n-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways (see, "Sequences of Proteins of Immunological Interest," Kabat, E., et al., U.S. Department of Health and Human Services, (1983); and Chothia and Lesk, *J. Mol. Biol.*, 196:901-917 (1987), which are incorporated herein by reference in their entireties).

Certain antibody molecules can also have effector functions mediated by binding of effector molecules. For example, binding of the C1 component of complement to an antibody activates the complement system. Activation of complement is important in the opsonization and lysis of cell pathogens. The activation of complement also stimulates the inflammatory response and can also be involved in autoimmune hypersensitivity. Further, certain antibodies can bind to cells via the Fc region of the antibody Fc region binding to an Fc receptor (FcR) on a cell. There are a number of Fc receptors which are specific for different classes of antibody, including, but not limited to, IgG (gamma receptors), IgE (eta receptors), IgA (alpha receptors) and IgM (mu receptors). Binding of antibody to Fc receptors on cell surfaces can trigger a number of important and diverse biological responses including, without limitation, engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer, and/or control of antibody production.

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. These particular regions have been described, for example, by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference. The Kabat and Chothia definitions include overlapping or subsets of amino acids when compared against each other. Nevertheless, application of either definition (or other definitions known to those of ordinary skill in the art) to refer to a CDR of an antibody or variant thereof is intended to be within the scope of the term as defined and used herein, unless otherwise indicated. The appropriate amino acids that encompass the CDRs as defined by each of the above cited references are set forth below in Table 1 as a comparison. The exact amino acid numbers that encompass a particular CDR will vary depending on the sequence and size of the CDR. Those skilled in the art can routinely determine that amino acids include a particular CDR given the variable region amino acid sequence of the antibody.

TABLE 1

| CDR Definitions* | | |
|---|---|---|
| | Kabat | Chothia |
| VH CDR1 | 31-35 | 26-32 |
| VH CDR2 | 50-65 | 52-58 |

TABLE 1-continued

| CDR Definitions* | | |
|---|---|---|
| | Kabat | Chothia |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

*Numbering of all CDR definitions in Table 1 is according to the numbering conventions set forth by Kabat et al. (see below).

Antibody variable domains can also be analyzed, e.g., using the IMGT information system (www://imgt.cines.fr/) (IMGT®/V-Quest) to identify variable region segments, including CDRs. (See, e.g., Brochet et al., *Nucl. Acids Res.*, 36:W503-508, 2008).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless use of the Kabat numbering system is explicitly noted, however, consecutive numbering is used for all amino acid sequences in this disclosure.

Binding molecules, e.g., antibodies or antigen binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), single domain antibodies such as camelid VHH antibodies, fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG$_1$, IgG$_2$, IgG$_3$, IgG$_4$, IgA$_1$ and IgA$_2$) or subclass of antibody molecule. Also contemplated are immunoglobulin new antigen receptor (IgNAR) isotypes (e.g., from sharks) that are bivalent and comprise a single chain that includes an IgNAR variable domain (VNAR). (See, Walsh et al., *Virology* 411:132-141, 2011).

By "specifically binds," it is generally meant that a binding molecule, e.g., an antibody or fragment, variant, or derivative thereof binds to an epitope via its antigen binding domain, and that the binding entails some complementarity between the antigen binding domain and the epitope. According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" can be deemed to have a higher specificity for a given epitope than binding molecule "B," or binding molecule "A" can be said to bind to epitope "C" with a higher specificity than it has for related epitope "D."

A binding molecule, e.g., an antibody or fragment, variant, or derivative thereof disclosed herein can be said to bind a target antigen with an off rate (k(off)) of less than or equal to $5 \times 10^{-2}$ sec$^{-1}$, $10^{-2}$ sec$^{-1}$, $5 \times 10^{-3}$ sec$^{-1}$, $10^{-3}$ sec$^{-1}$, $5 \times 10^{-4}$ sec$^{-1}$, 10$^{-4}$ sec$^{-1}$, 5×10$^{-5}$ sec$^{-1}$, or 10$^{-5}$ sec$^{-1}$ 5×10$^{-6}$ sec$^{-1}$, 10$^{-6}$ sec$^{-1}$, 5×10$^{-7}$ sec$^{-1}$ or 10$^{-7}$ sec$^{-1}$.

A binding molecule, e.g., an antibody or antigen binding fragment, variant, or derivative disclosed herein can be said to bind a target antigen with an on rate (k(on)) of greater than or equal to 10$^3$ M$^{-1}$ sec$^{-1}$, 5×10$^3$ M$^{-1}$ sec$^{-1}$, 10$^4$ M$^{-1}$ sec$^{-1}$, 5×10$^4$ M$^{-1}$ sec$^{-1}$, 10$^5$ M$^{-1}$ sec$^{-1}$, 5×10$^5$ M$^{-1}$ sec$^{-1}$, 10$^6$ M$^{-1}$ sec$^{-1}$, or 5×10$^6$ M$^{-1}$ sec$^{-1}$ or 10$^7$ M$^{-1}$ sec$^{-1}$.

A binding molecule, e.g., an antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with one or more antigen binding domains, e.g., of an antibody molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of antigen binding domains and an antigen. See, e.g., Harlow at pages 29-34. Avidity is related to both the affinity of individual antigen binding domains in the population with specific epitopes, and also the valencies of the antibody and the antigen. For example, the interaction between a bivalent monoclonal antibody and an antigen with a highly repeating epitope structure, such as a polymer, would be one of high avidity. An interaction between a between a bivalent monoclonal antibody with a receptor present at a high density on a cell surface would also be of high avidity.

Binding molecules or antigen binding fragments, variants or derivatives thereof as disclosed herein can also be described or specified in terms of their cross-reactivity. As used herein, the term "cross-reactivity" refers to the ability of a binding molecule, e.g., an antibody or fragment, variant, or derivative thereof, specific for one antigen, to react with a second antigen; a measure of relatedness between two different antigenic substances. Thus, a binding molecule is cross reactive if it binds to an epitope other than the one that induced its formation. The cross reactive epitope generally contains many of the same complementary structural features as the inducing epitope, and in some cases, can actually fit better than the original.

A binding molecule, e.g., an antibody or fragment, variant, or derivative thereof can also be described or specified in terms of its binding affinity to an antigen. For example, a binding molecule can bind to an antigen with a dissociation constant or K$_D$ no greater than 5×10$^{-2}$ M, 10$^{-2}$ M, 5×10$^{-3}$ M, 10$^{-3}$ M, 5×10$^{-4}$ M, 10$^{-4}$ M, 5×10$^{-5}$ M, 10$^{-5}$ M, 5×10$^{-6}$ M, 10$^{-6}$ M, 5×10$^{-7}$ M, 10$^{-7}$ M, 5×10$^{-8}$ M, 10$^{-8}$ M, 5×10$^{-9}$ M, 10$^{-9}$ M, 5×10$^{-10}$ M, 10$^{-10}$ M, 5×10$^{-11}$ M, 10$^{-11}$ M, 5×10$^{-12}$ M, 10$^{-12}$ M, 5×10$^{-13}$ M, 10$^{-13}$ M, 5×10$^{-14}$ M, 10$^{-14}$ M, 5×10$^{-15}$ M, or 10$^{-15}$ M.

Antibody fragments including single-chain antibodies or other antigen binding domains can exist alone or in combination with one or more of the following: hinge region, CH1, CH2, CH3, or CH4 domains, J-chain, or secretory component. Also included are antigen binding fragments that can include any combination of variable region(s) with one or more of a hinge region, CH1, CH2, CH3, or CH4 domains, a J-chain, or a secretory component. Binding molecules, e.g., antibodies, or antigen binding fragments thereof can be from any animal origin including birds and mammals. The antibodies can be human, murine, donkey, rabbit, goat, guinea pig, camel, llama, horse, or chicken antibodies. In another embodiment, the variable region can be condricthoid in origin (e.g., from sharks). As used herein, "human" antibodies include antibodies having the amino acid sequence of a human antibody and include antibodies isolated from human antibody libraries or from animals transgenic for one or more human antibodies and can in some instances express endogenous immunoglobulins and some not, as described infra and, for example in, U.S. Pat. No. 5,939,598 by Kucherlapati et al.

As used herein, the term "heavy chain subunit" or "heavy chain domain" includes amino acid sequences derived from an antibody heavy chain, a binding molecule, e.g., an antibody comprising a heavy chain subunit can include at least one of: a VH domain, a CH1 domain, a hinge (e.g., upper, middle, and/or lower hinge region) domain, a CH2 domain, a CH3 domain, a CH4 domain, or a variant or fragment thereof.

The heavy chain subunits of a binding molecule, e.g., an antibody or fragment thereof, can include domains derived from different antibody molecules. For example, a heavy chain subunit of a polypeptide can include a CH1 domain derived from an IgG$_1$ molecule and a hinge region derived from an IgG$_3$ molecule. In another example, a heavy chain subunit can include a hinge region derived, in part, from an IgG$_1$ molecule and, in part, from an IgG$_3$ molecule. In another example, a heavy chain subunit can comprise a chimeric hinge derived, in part, from an IgG$_1$ molecule and, in part, from an IgG$_4$ molecule.

As used herein, the term "light chain subunit" or "light chain domain" includes amino acid sequences derived from an antibody light chain. The light chain subunit includes at least one of a VL or CL (e.g., Cκ or Cλ) domain.

Binding molecules, e.g., antibodies or antigen binding fragments, variants, or derivatives thereof can be described or specified in terms of the epitope(s) or portion(s) of an antigen that they recognize or specifically bind. The portion of a target antigen that specifically interacts with the antigen binding domain of an antibody is an "epitope," or an "antigenic determinant." A target antigen can comprise a single epitope or at least two epitopes, and can include any number of epitopes, depending on the size, conformation, and type of antigen.

As used herein, the term "chimeric antibody" refers to an antibody in which the immunoreactive region or site is obtained or derived from a first species and the constant region (which can be intact, partial or modified) is obtained from a second species. In some embodiments the target binding region or site will be from a non-human source (e.g. mouse or primate) and the constant region is human.

The terms "multispecific antibody, or "bispecific antibody" refer to an antibody that has antigen binding domains that are specific for two or more different epitopes within a single antibody molecule. Other binding molecules in addition to the canonical antibody structure can be constructed with two different binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, *IDrugs.* 13:543-9 (2010)). A bispecific antibody can also be a diabody. Thus, a bispecific binding molecule that is multimeric could potentially possess several different antigen binding domains, each with a different specificity.

As used herein, the term "engineered antibody" refers to an antibody in which the variable domain in either the heavy and light chain or both is altered by at least partial replacement of one or more amino acids in either the CDR or framework regions. In certain aspects entire CDRs from an antibody of known specificity can be grafted into the framework regions of a heterologous antibody. Although alternate CDRs can be derived from an antibody of the same class or even subclass as the antibody from which the framework regions are derived, CDRs can also be derived from an antibody of different class, e.g., from an antibody from a different species. An engineered antibody in which one or more "donor" CDRs from a non-human antibody of known specificity are grafted into a human heavy or light chain framework region is referred to herein as a "humanized antibody." In certain aspects not all of the CDRs are replaced with the complete CDRs from the donor variable region and yet the antigen binding capacity of the donor can still be transferred to the recipient variable domains. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

As used herein, the terms "linked," "fused" or "fusion" or other grammatical equivalents can be used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the translational reading frame of the original ORFs. Thus, a recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence. For example, polynucleotides encoding the CDRs of an antibody variable region can be fused, in-frame, but be separated by a polynucleotide encoding at least one antibody framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which amino acids that neighbor each other in the sequence are contiguous in the primary structure of the polypeptide.

A portion of a polypeptide that is "amino-terminal" or "N-terminal" to another portion of a polypeptide is that portion that comes earlier in the sequential polypeptide chain. Similarly, a portion of a polypeptide that is "carboxy-terminal" or "C-terminal" to another portion of a polypeptide is that portion that comes later in the sequential polypeptide chain. For example, in a typical antibody, the variable domain is "N-terminal" to the constant region, and the constant region is "C-terminal" to the variable domain.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide that is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "eukaryote" or "eukaryotic organism" is intended to encompass all organisms in the animal, plant, and protist kingdoms, including protozoa, fungi, yeasts, green algae, single celled plants, multi celled plants, and all animals, both vertebrates and invertebrates. The term does not encompass bacteria or viruses. A "eukaryotic cell" is intended to encompass a singular "eukaryotic cell" as well as plural "eukaryotic cells," and comprises cells derived from a eukaryote.

The term "vertebrate" is intended to encompass a singular "vertebrate" as well as plural "vertebrates," and comprises mammals and birds, as well as fish, reptiles, and amphibians.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In certain aspects the mammal is a human subject.

The terms "tissue culture" or "cell culture" or "culture" or "culturing" refer to the maintenance or growth of plant or animal tissue or cells in vitro under conditions that allow preservation of cell architecture, preservation of cell function, further differentiation, or all three. "Primary tissue cells" are those taken directly from tissue, i.e., a population of cells of the same kind performing the same function in an organism. Treating such tissue cells with the proteolytic enzyme trypsin, for example, dissociates them into individual primary tissue cells that grow or maintain cell architecture when seeded onto culture plates. Cell cultures arising from multiplication of primary cells in tissue culture are called "secondary cell cultures." Most secondary cells divide a finite number of times and then die. A few secondary cells, however, can pass through this "crisis period," after which they are able to multiply indefinitely to form a continuous "cell line." The liquid medium in which cells are cultured is referred to herein as "culture medium" or "culture media." Culture medium into which desired molecules, e.g., viruses or proteins, e.g., antibody molecules, have been secreted during culture of the cells therein can be referred to as "conditioned medium."

As used herein, the term "identify" refers to methods in which a desired molecule, e.g., a polynucleotide encoding a protein of interest with a desired characteristics or function, is differentiated from a plurality or library of such molecules. Identification methods include "selection" and "screening" or "panning." As used herein, "selection" methods are those in which the desired molecules can be directly separated from the library. As used herein, "screening" or "panning" methods are those in which pools comprising the desired molecules are subjected to an assay in which the desired molecule can be detected. Aliquots of the pools in which the molecule is detected are then divided into successively smaller pools which are likewise assayed, until a pool which is highly enriched from the desired molecule is achieved.

Poxvirus Vectors

Libraries of polynucleotides constructed according to the methods provided herein can be constructed in a poxvirus vector. "Poxvirus" includes any member of the family Poxviridae, including the subfamilies Chordopoxviridae (vertebrate poxviruses) and Entomopoxviridae (insect poxviruses). See, for example, B. Moss in: *Virology, 2d Edition*, B. N. Fields, D. M. Knipe et al., Eds., Raven Press, p. 2080 (1990). The chordopoxviruses comprise, inter alia, the following genera: Orthopoxvirus (e.g., vaccinia, variola virus, raccoon poxvirus); Avipoxvirus (e.g., fowlpox); Capripoxvirus (e.g., sheeppox) Leporipoxvirus (e.g., rabbit (Shope) fibroma, and myxoma); and Suipoxvirus (e.g., swinepox). The entomopoxviruses comprise three genera: A, B and C. Vaccinia virus is the prototype orthopoxvirus, and has been developed and is well-characterized as a vector for the expression of heterologous proteins.

Poxviruses are distinguished by their large size and complexity, and contain similarly large and complex genomes. Notably, poxviruses replication takes place entirely within the cytoplasm of a host cell. The central portions of poxvirus genomes are similar, while the terminal portions of the virus genomes are characterized by more variability. Accordingly, it is thought that the central portion of poxvirus genomes carry genes responsible for essential functions common to all poxviruses, such as replication. By contrast, the terminal portions of poxvirus genomes appear responsible for characteristics such as pathogenicity and host range, which vary among the different poxviruses, and can be more likely to be non-essential for virus replication in tissue culture. It follows that if a poxvirus genome is to be modified by the rearrangement or removal of DNA fragments or the introduction of exogenous DNA fragments, the portion of the naturally-occurring DNA which is rearranged, removed, or disrupted by the introduction of exogenous DNA can be in regions thought to be non-essential for replication of the virus and production if infectious virions in tissue culture, e.g., the more distal regions.

The naturally-occurring vaccinia virus genome is a cross-linked, double stranded linear DNA molecule, of about 186,000 base pairs (bp), which is characterized by inverted terminal repeats. The genome of vaccinia virus has been completely sequenced, and a variety of non-essential regions have been identified in the vaccinia virus genome. See, e.g., Perkus, M. E., et al., *Virology* 152:285-97 (1986); and Kotwal, G. J. and Moss B., *Virology* 167:524-37. The most widely used non-essential region for insertion of foreign genes into vaccinia virus is the thymidine kinase locus, located in the HindIII J fragment in the genome. In certain vaccinia virus vectors, the tk locus has been engineered to contain one or two unique restriction enzyme sites, allowing for convenient use of the trimolecular recombination method of library generation. See infra, and also Zauderer, PCT Publication No. WO 00/028016.

Libraries of polynucleotides encoding polypeptides of interest, e.g., antibody subunit polypeptides, can be inserted into poxvirus vectors, e.g., vaccinia virus vectors, under operable association with a transcriptional control region which functions in the cytoplasm of a poxvirus-infected cell.

Poxvirus transcriptional control regions comprise a promoter and a transcription termination signal. Gene expression in poxviruses is temporally regulated, and promoters for early, intermediate, and late genes possess varying structures. Certain poxvirus genes are expressed constitutively, and promoters for these "early-late" genes bear hybrid structures. Synthetic early-late promoters have also been developed. See Hammond J. M., et al., *J. Virol. Methods* 66:135-8 (1997); Chakrabarti S., et al., *Biotechniques* 23:1094-7 (1997). Any poxvirus promoter can be used in the methods provided herein.

Examples of early promoters include the 7.5-kD promoter (also a late promoter), the DNA pol promoter, the tk promoter, the RNA pol promoter, the 19-kD promoter, the 22-kD promoter, the 42-kD promoter, the 37-kD promoter, the 87-kD promoter, the H3' promoter, the H6 promoter, the D1 promoter, the D4 promoter, the D5 promoter, the D9 promoter, the D12 promoter, the 13 promoter, the M1 promoter, and the N2 promoter. See, e.g., Moss, B., "Poxviridae and their Replication" IN *Virology, 2d Edition*, B. N. Fields, D. M. Knipe et al., Eds., Raven Press, p. 2088 (1990). Early genes transcribed in vaccinia virus and other poxviruses recognize the transcription termination signal TTTTTNT, where N can be any nucleotide. Transcription normally terminates approximately 50 bp upstream of this signal. Accordingly, if heterologous genes are to be expressed from poxvirus early promoters, care must be taken to eliminate occurrences of this signal in the coding regions for those genes. See, e.g., Earl, P. L., et al., *J. Virol.* 64:2448-51 (1990).

Example of late promoters include the 7.5-kD promoter, the MIL promoter, the 37-kD promoter, the 11-kD promoter, the 11L promoter, the 12L promoter, the 13L promoter, the 15L promoter, the 17L promoter, the 28-kD promoter, the H1L promoter, the H3L promoter, the H5L promoter, the H6L promoter, the H8L promoter, the D11L promoter, the D12L promoter, the D13L promoter, the AIL promoter, the A2L promoter, the A3L promoter, and the P4b promoter. See, e.g., Moss, B., "Poxviridae and their Replication" IN *Virology*, 2d Edition, B. N. Fields, D. M. Knipe et al., Eds., Raven Press, p. 2090 (1990). The late promoters apparently do not recognize the transcription termination signal recognized by early promoters.

Constitutive promoters for use in the methods provided herein can include the synthetic early-late promoters described by Hammond and Chakrabarti, the MH-5 early-late promoter, and the 7.5-kD or "p7.5" promoter.

A number of attenuated poxviruses, in particular vaccinia viruses, have been developed, and have been used as vectors. For example, modified vaccinia Ankara (MVA) is a highly attenuated strain of vaccinia virus that was derived during over 570 passages in primary chick embryo fibroblasts (Mayr, A. et al., *Infection* 3:6-14 (1975)). The recovered virus deleted approximately 15% of the wild type vaccinia DNA which profoundly affects the host range restriction of the virus. MVA cannot replicate or replicates very inefficiently in most mammalian cell lines. A unique feature of the host range restriction is that the block in non-permissive cells occurs at a relatively late stage of the replication cycle. Expression of viral late genes is relatively unimpaired, but virion morphogenesis is interrupted (Suter, G. and Moss, B., *Proc Natl Acad Sci USA* 89:10847-51

(1992); Carroll, M. W. and Moss, B., Virology 238:198-211 (1997)). The high levels of viral protein synthesis even in non-permissive host cells make MVA an especially safe and efficient expression vector. However, because MVA cannot complete the infectious cycle in most mammalian cells, in order to recover infectious virus for multiple cycles of selection it will be necessary to complement the MVA deficiency by coinfection or superinfection with a helper virus that is itself deficient and that can be subsequently separated from infectious MVA recombinants by differential expansion at low MOI in MVA permissive host cells.

As used herein, the term "complementation" refers to a restoration of a lost function in trans by another source, such as a host cell, transgenic animal or helper virus. The loss of function is caused by loss by the defective virus of the gene product responsible for the function. Thus, a defective poxvirus is a non-viable form of a parental poxvirus, and is a form that can become viable in the presence of complementation. The host cell, transgenic animal or helper virus contains the sequence encoding the lost gene product, or "complementation element." The complementation element can, in some aspects, be expressible and stably integrated in the host cell, transgenic animal or helper virus, and in certain aspects is engineered so as to provide little or no risk for recombination with the genome of the defective poxvirus.

Viruses produced in the complementing cell line are capable of infecting non-complementing cells, and further are capable of high-level expression of early gene products. However, in the absence of the essential gene product, host shut-off, DNA replication, packaging, and production of infectious virus particles does not take place.

The Tri-Molecular Recombination Method

Traditionally, poxvirus vectors such as vaccinia virus were not used to identify previously unknown genes of interest from complex libraries because a high efficiency, high complexity, high titer-producing method of constructing and screening libraries did not exist for vaccinia. The traditional method of heterologous protein expression in vaccinia virus involved in vivo homologous recombination between a transfer plasmid and an intact vaccinia virus genome, and in vitro direct ligation. Using traditional homologous recombination, the efficiency of recombinant virus production was in the range of approximately 0.1% or less. Although efficiency of recombinant virus production using direct ligation is higher, the resulting titer is relatively low. Thus, the use of vaccinia virus vectors was limited to the cloning of previously isolated DNA for the purposes of protein expression and vaccine development.

Tri-molecular recombination, as disclosed in Zauderer, PCT Publication No. WO 00/028016, is a high efficiency, high titer-producing method for producing recombinant poxvirus, e.g., recombinant vaccinia virus. The tri-molecular recombination method allows the generation of recombinant viruses at efficiencies of at least 90%, and titers at least at least 2 orders of magnitude higher than those obtained by direct ligation. Given this high efficiency, libraries of polynucleotides capable of expressing polypeptides of interest, e.g., antibody subunit polypeptides, can constructed in poxvirus vectors, e.g., vaccinia virus vectors, using tri-molecular recombination.

By "tri-molecular recombination" or a "tri-molecular recombination method" is meant a method of producing a modified virus genome, e.g., a poxvirus genome, e.g., a vaccinia virus genome, comprising a heterologous polynucleotide of interest, by introducing two nonhomologous fragments of a virus genome, i.e., two virus genome "arms" that are incapable of undergoing homologous recombination with each other, and a transfer vector or transfer DNA containing the polynucleotide of interest into a recipient cell, and allowing the three DNA molecules to recombine in vivo. As a result of the recombination, a viable virus genome is produced which comprises each of the two genome fragments and the polynucleotide of interest. Thus, the trimolecular recombination method as described herein can comprise: (a) cleaving an isolated poxvirus genome, e.g., a vaccinia virus genome, to produce a first viral fragment and a second viral fragment, where the first viral fragment is incapable of undergoing homologous recombination with the second viral fragment; (b) providing a population of transfer plasmids comprising polynucleotides of interest that encode polypeptides of interest, e.g., antibody subunit polypeptides, e.g., antibody light chains, antibody heavy chains, or antigen-specific fragments of either, through operable association with a transcription control region, flanked by a 5' flanking region and a 3' flanking region, where the 5' flanking region comprises a region homologous to the 3' end of the first viral fragment and the 3' flanking region comprises a region homologous to the 5' end of the second viral fragment; and where the transfer plasmids are capable of homologous recombination with the first and second viral fragments such that a viable virus genome can be formed; (c) introducing the transfer plasmids described in (b) and the first and second viral fragments described in (a) into a host cell under conditions where a transfer plasmid and the two viral fragments can undergo in vivo homologous recombination, i.e., trimolecular recombination, thereby producing a viable modified virus genome comprising a polynucleotide which encodes a polypeptide of interest, e.g., an antibody subunit polypeptide; (d) adding an inhibitor of poxvirus assembly, e.g., rifampicin as described elsewhere herein, and recovering modified virus genomes produced by this technique. In certain aspects, the recovered modified poxvirus genome can be packaged in an infectious viral particle.

By "recombination efficiency" or "efficiency of recombinant virus production" is meant the ratio of recombinant virus to total virus produced during the generation of virus libraries by the methods provided herein. The efficiency can be calculated by dividing the titer of recombinant virus by the titer of total virus and multiplying by 100%. For example, the titer can be determined by plaque assay of crude virus stock on appropriate cells either with selection (e.g., for recombinant virus) or without selection (e.g., for recombinant virus plus wild type virus). Methods of selection, particularly if heterologous polynucleotides are inserted into the viral thymidine kinase (tk) locus, are well-known in the art and include resistance to bromodeoxyuridine (BDUR) or other nucleotide analogs due to disruption of the tk gene. Examples of selection methods are described herein.

By "high efficiency recombination" is meant a recombination efficiency of at least about 1%, 2%, 2.5%, 3%, 3.5%, 4%, 5%, 10%, 20%, 30%, 40%, 50%, 60%, 70%, 75%, 80%, 85%, 90%, 95%, or 99%.

A number of selection systems can be used, including but not limited to the thymidine kinase such as herpes simplex virus thymidine kinase (Wigler, et al., 1977, Cell 11:223), hypoxanthine-guanine phosphoribosyl transferase (Szybalska & Szybalski, 1962, Proc. Natl. Acad. Sci. USA 48:2026), and adenine phosphoribosyl transferase (Lowy, et al., 1980, Cell 22:817) genes which can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Proc. Natl. Acad. Sci. USA 77:3567; O'Hare, et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, *Gene* 30:147).

Together, the first and second viral fragments or "arms" of the virus genome, as described above typically contain all the genes necessary for viral replication and for production of infectious viral particles. Examples of suitable arms and methods for their production using vaccinia virus vectors are disclosed herein. See also Falkner et al., U.S. Pat. No. 5,770,212 for guidance concerning essential regions for vaccinia replication.

However, naked poxvirus genomic DNAs such as vaccinia virus genomes cannot produce infectious progeny without virus-encoded protein protein(s)/function(s) associated with the incoming viral particle. The required virus-encoded functions, include an RNA polymerase that recognizes the transfected vaccinia DNA as a template, initiates transcription and, ultimately, replication of the transfected DNA. See Dorner, et al. U.S. Pat. No. 5,445,953.

Thus, to produce infectious progeny virus by trimolecular recombination using a poxvirus such as vaccinia virus, the recipient cell can contain packaging functions. The packaging functions can be provided by helper virus, e.g., a virus that, together with the transfected naked genomic DNA, provides appropriate proteins and factors necessary for replication and assembly of progeny virus.

The helper virus can be a closely related virus, for instance, a poxvirus of the same poxvirus subfamily as vaccinia, whether from the same or a different genus. In such a case it is advantageous to select a helper virus which provides an RNA polymerase that recognizes the transfected DNA as a template and thereby serves to initiate transcription and, ultimately, replication of the transfected DNA. If a closely related virus is used as a helper virus, it is advantageous that it be attenuated such that formation of infectious virus will be impaired. For example, a temperature sensitive helper virus can be used at the non-permissive temperature. In certain aspects a heterologous helper virus is used. Examples include, but are not limited to an avipox virus such as fowlpox virus, or an ectromelia virus (mouse pox) virus. Avipoxviruses provide the necessary helper functions, but do not replicate, or produce infectious virions in mammalian cells (Scheiflinger, et al., *Proc. Natl. Acad. Sci. USA* 89:9977-9981 (1992)). Use of heterologous viruses minimizes recombination events between the helper virus genome and the transfected genome which take place when homologous sequences of closely related viruses are present in one cell. See Fenner & Comben, *Virology* 5:530 (1958); Fenner, *Virology* 8:499 (1959).

Alternatively, the necessary helper functions in the recipient cell can be supplied by a genetic element other than a helper virus. For example, a host cell can be transformed to produce the helper functions constitutively, or the host cell can be transiently transfected with a plasmid expressing the helper functions, infected with a retrovirus expressing the helper functions, or provided with any other expression vector suitable for expressing the required helper virus function. See Dorner, et al. U.S. Pat. No. 5,445,953.

According to the trimolecular recombination method, the first and second viral genomic fragments are unable to ligate or recombine with each other, i.e., they do not contain compatible cohesive ends or homologous regions, or alternatively, cohesive ends have been treated with a dephosphorylating enzyme. In certain aspects, a virus genome can comprise a first recognition site for a first restriction endonuclease and a second recognition site for a second restriction endonuclease, and the first and second viral fragments are produced by digesting the viral genome with the appropriate restriction endonucleases to produce the viral "arms," and the first and second viral fragments are isolated by standard methods. Ideally, the first and second restriction endonuclease recognition sites are unique in the viral genome, or alternatively, cleavage with the two restriction endonucleases results in viral "arms" which include the genes for all essential functions, i.e., where the first and second recognition sites are physically arranged in the viral genome such that the region extending between the first and second viral fragments is not essential for virus infectivity.

Where a vaccinia virus vector is used in the trimolecular recombination method, a vaccinia virus vector comprising a virus genome with two unique restriction sites within the tk gene can be used. For example, the first restriction enzyme can be NotI, having the recognition site GCGGCCGC in the tk gene, and the second restriction enzyme can be ApaI, having the recognition site GGGCCC in the tk gene. Exemplary vaccinia virus vectors include a v7.5/tk virus genome or a vEL/tk virus genome. Merchlinsky, et al., *Virology* 238:444-451 (1997).

According to this embodiment, a transfer plasmid with flanking regions capable of homologous recombination with the region of the vaccinia virus genome containing the thymidine kinase gene is used. A fragment of the vaccinia virus genome comprising the HindIII-J fragment, which contains the tk gene, is conveniently used.

In certain aspects, the polynucleotides of interest can be operably associated with poxvirus expression control sequences, e.g., strong constitutive poxvirus promoters such as p7.5 or a synthetic early/late promoter.

Accordingly, a transfer plasmid as provided herein can comprise a polynucleotide encoding a protein of interest, e.g., an antibody subunit polypeptide, e.g., a heavy chain, a light chain, or an antigen-binding fragment of a heavy chain or a light chain, through operable association with a vaccinia virus p7.5 promoter, or a synthetic early/late promoter. The transfer plasmid can be any of the transfer plasmids described in PCT Publication No. WO 00/028016, U.S. Pat. No. 6,706,477, or U.S. Pat. No. 7,858,559, which are incorporated herein by reference in their entireties.

In one aspect, a transfer plasmid comprising a polynucleotide encoding a protein of interest, e.g., an antibody heavy chain polypeptide, through operable association with a vaccinia virus p7.5 promoter can be pVHE, which comprises the sequence, designated herein as SEQ ID NO: 1:

```
GGCCAAAAATTGAAAAACTAGATCTATTTATTGCACGCG

GCCGCAAACCATGGGATGGAGCTGTATCATCCTCTTCTTG

GTAGCAACAGCTACAGGCGCGCATATGGTCACCGTCTC

CTCAGGGAGTGCATCCGCCCCAACCCTTTTCCCCCTCGTC

TCCTGTGAGAATTCCCCGTCGGATACGAGCAGCGTGGCC

GTTGGCTGCCTCGCACAGGACTTCCTTCCCGACTCCATCA

CTTTCTCCTGGAAATACAAGAACAACTCTGACATCAGCA

GCACCCGGGGCTTCCCATCAGTCCTGAGAGGGGCAAGT

ACGCAGCCACCTCACAGGTGCTGCTGCCTTCCAAGGACG
```

```
TCATGCAGGGCACAGACGAACACGTGGTGTGCAAAGTCC

AGCACCCCAACGGCAACAAAGAAAAGAACGTGCCTCTTC

CAGTGATTGCTGAGCTGCCTCCCAAAGTGAGCGTCTTCGT

CCCACCCCGCGACGGCTTCTTCGGCAACCCCCGCAGCAA

GTCCAAGCTCATCTGCCAGGCCACGGGTTTCAGTCCCCG

GCAGATTCAGGTGTCCTGGCTGCGCGAGGGGAAGCAGGT

GGGGTCTGGCGTCACCACGGACCAGGTGCAGGCTGAGGC

CAAAGAGTCTGGGCCCACGACCTACAAGGTGACTAGCAC

ACTGACCATCAAAGAGAGCGACTGGCTCAGCCAGAGCAT

GTTCACCTGCCGCGTGGATCACAGGGGCCTGACCTTCCA

GCAGAATGCGTCCTCCATGTGTGTCCCCGATCAAGACAC

AGCCATCCGGGTCTTCGCCATCCCCCCATCCTTTGCCAGC

ATCTTCCTCACCAAGTCCACCAAGTTGACCTGCCTGGTCA

CAGACCTGACCACCTATGACAGCGTCACCATCTCCTGGA

CCCGCCAGAATGGCGAAGCTGTGAAAACCCACACCAACA

TCTCCGAGAGCCACCCCAATGCCACTTTCAGCGCCGTGG

GTGAGGCCAGCATCTGCGAGGATGACTGGAATTCCGGGG

AGAGGTTCACGTGCACCGTGACCCACACAGACCTGCCCT

CGCCACTGAAGCAGACCATCTCCCGGCCCAAGGGGGTGG

CCCTGCACAGGCCCGATGTCTACTTGCTGCCACCAGCCC

GGGAGCAGCTGAACCTGCGGGAGTCGGCCACCATCACGT

GCCTGGTGACGGGCTTCTCTCCCGCGGACGTCTTCGTGCA

GTGGATGCAGAGGGGGCAGCCCTTGTCCCCGGAGAAGTA

TGTGACCAGCGCCCCAATGCCTGAGCCCCAGGCCCCAGG

CCGGTACTTCGCCCACAGCATCCTGACCGTGTCCGAAGA

GGAATGGAACACGGGGGAGACCTACACCTGCGTGGTGGC

CCATGAGGCCCTGCCCAACAGGGTCACTGAGAGGACCGT

GGACAAGTCCACCGAGGGGGAGGTGAGCGCCGACGAGG

AGGGCTTTGAGAACCTGTGGGCCACCGCCTCCACCTTCAT

CGTCCTCTTCCTCCTGAGCCTCTTCTACAGTACCACCGTC

ACCTTGTTCAAGGTGAAATGAGTCGAC
```

PCR-amplified heavy chain variable regions can be inserted in-frame into unique BssHII, and/or BstEII sites, which are indicated above in bold.

In another aspect, a transfer plasmid comprising a polynucleotide encoding a protein of interest, e.g., an antibody light chain polypeptide, through operable association with a vaccinia virus p7.5 promoter can be pVKE, which comprises the sequence, designated herein as SEQ ID NO: 2:

```
GGCCAAAAATTGAAAAACTAGATCTATTTATTGCACGCG

GCCGCCCATGGGATGGAGCTGTATCATCCTCTTCTTGGTA

GCAACAGCTACACGGGTGCACTTGACTCGAGATCAAAC

GAACTGTGGCTGCACCATCTGTCTTCATCTTCCCGCCATC

TGATGAGCAGTTGAAATCTGGAACTGCCTCTGTTGTGTGC

CTGCTGAATAACTTCTATCCCAGAGAGGCCAAAGTACAG

TGGAAGGTGGATAACGCCCTCCAATCGGGTAACTCCCAG

GAGAGTGTCACAGAGCAGGACAGCAAGGACAGCACCTA

CAGCCTCAGCAGCACCCTGACGCTGAGCAAAGCAGACTA

CGAGAAACACAAAGTCTACGCCTGCGAAGTCACCCATCA

GGGCCTGAGCTCGCCCGTCACAAAGAGCTTCAACAGGGG

AGAGTGTTAGGTCGAC
```

PCR-amplified kappa light chain variable regions can be inserted in-frame into unique ApaLI and/or XhoI sites, which are indicated above in bold.

In another aspect, a transfer plasmid comprising a polynucleotide encoding a protein of interest, e.g., an antibody light chain polypeptide, through operable association with a vaccinia virus p7.5 promoter can be pVLE, which comprises the sequence, designated herein as SEQ ID NO: 3:

```
GGCCAAAAATTGAAAAACTAGATCTATTTATTGCACGCG

GCCGCCCATGGGATGGAGCTGTATCATCCTCTTCTTGGTA

GCAACAGCTACAGGCGTGCACTTGACTCGAGAAGCTTA

CCGTCCTACGAACTGTGGCTGCACCATCTGTCTTCATCTT

CCCGCCATCTGATGAGCAGTTGAAATCTGGAACTGCCTCT

GTTGTGTGCCTGCTGAATAACTTCTATCCCAGAGAGGCCA

AAGTACAGTGGAAGGTGGATAACGCCCTCCAATCGGGTA

ACTCCCAGGAGAGTGTCACAGAGCAGGACAGCAAGGAC

AGCACCTACAGCCTCAGCAGCACCCTGACGCTGAGCAAA

GCAGACTACGAGAAACACAAAGTCTACGCCTGCGAAGTC

ACCCATCAGGGCCTGAGCTCGCCCGTCACAAAGAGCTTC

AACAGGGGAGAGTGTTAGGTCGAC
```

PCR-amplified lambda light chain variable regions can be inserted in-frame into unique ApaLI and/or HindIII sites, which are indicated above in bold.

By "insert DNA" or "polynucleotide of interest" is meant one or more heterologous DNA segments to be expressed in a recombinant poxvirus vector. "Polynucleotides of interest" as used herein are polynucleotides that encode proteins of interest, e.g., antibody subunit polypeptides. A polynucleotide of interest can be naturally occurring, non-naturally occurring, synthetic, or a combination thereof. Methods of producing polynucleotides of interest for use in the methods provided herein are well known by persons of skill in the art.

By "transfer plasmid" is meant a plasmid vector containing a polynucleotide of interest positioned between a 5' flanking region and a 3' flanking region as described above. The 5' flanking region shares homology with the first viral fragment, and the 3' flanking region shares homology with the second viral fragment. In certain aspects, the transfer plasmid contains a suitable promoter, such as a strong, constitutive vaccinia promoter, upstream of the polynucleotide of interest. The term "vector" means a polynucleotide construct containing a heterologous polynucleotide segment, which is capable of effecting transfer of that polynucleotide segment into a suitable host cell. In certain aspects the polynucleotide contained in the vector is operably linked to a suitable control sequence capable of effecting the expression of the polynucleotide in a suitable host. Such control sequences include a promoter to effect transcription, an optional operator sequence to control such transcription, a sequence encoding suitable mRNA ribosome binding sites, and sequences which control the termination of transcription and translation. As used herein, a vector can be a plasmid, a phage particle, a virus, a messenger RNA, or simply a potential genomic insert. Once transformed into a suitable host, the vector can replicate and function independently of the host genome, or can in some instances, integrate into the genome itself. Typical plasmid expression vectors for mammalian cell culture expression, for example, are based on pRK5 (EP 307,247), pSV16B (WO 91/08291) and pVL1392 (Pharmingen).

However, "a transfer plasmid," as used herein, is not limited to a specific plasmid or vector. Any DNA segment in circular or linear or other suitable form can act as a vehicle for transferring the DNA insert into a host cell along with the first and second viral "arms" in the tri-molecular recombination method. Other suitable vectors include lambda phage, mRNA, DNA fragments, etc., as described herein or otherwise known in the art. A plurality of plasmids can be a "primary library" such as those described herein for lambda.

Addition of an Inhibitor of Vaccinia Virus Assembly

In accordance with the methods provided herein, an inhibitor of vaccinia virus assembly can be added to improve the complexity, diversity, and/or titer of the poxvirus libraries that are constructed using tri-molecular recombination. One such inhibitor is rifampicin. Rifampicin is an antibiotic that is typically used to treat various bacterial infections. Rifampicin inhibits bacterial RNA polymerase, making it able to inhibit the synthesis of host bacterial proteins during recombinant protein expression in bacteria. It is also able to reversibly inhibit the replication of vaccinia virus by preventing the assembly of DNA and proteins into mature virus participles (Moss., B., et al., *Nature* 224: 1280-1284 (1969)). Other inhibitors of poxvirus assembly can include, without limitation, azathioprine, novobiocin, and/or mitoxantrone.

While inhibiting virus growth is beneficial in instances where the speed of replication needs to be reduced, such as in spontaneous recombination, tri-molecular recombination requires the viral genome to be reassembled in order to yield virus. It is, therefore, unexpected that the addition of an inhibitor such as rifampicin would improve the quality, complexity and/or titer of the recombinants that are constructed using tri-molecular recombination. However, the methods provided herein can delay total virus growth until after recombination takes place. For example, rifampicin can be added following transfection, e.g., at about 6 hours, about 12 hours, about 18 hours, about 24 hours, about 30 hours, about 36 hours, about 42 hours, about 48 hours, about 54 hours, or about 60 hours following transfection, to increase the number of individual (unique) recombinants that are constructed, by both extending the time period for recombination to occur, and by preventing packaged virus from over growing the cultures. In certain aspects, rifampicin or a derivative thereof can be added to the cell culture medium at a concentration of about 30 µg/ml, about 40 µg/ml, about 50 µg/ml, about 60 µg/ml, about 70 µg/ml, about 80 µg/ml, about 90 µg/ml, about 100 µg/ml, about 110 µg/ml, about 120 µg/ml, or about 130 µg/ml. In certain aspects the rifampicin or derivative thereof can be maintained in the cell culture medium for about one day, about two days, about three days, about four days or about five days. Following incubation of the transfected cells with cell culture medium comprising rifampicin, the cell culture medium can be replaced with cell culture medium without rifampicin, and the transfected host cells can be further cultured without rifampicin for, e.g., about one day, about two days, or about three days.

The methods of library construction provided herein can result in an increased number of independent modified poxvirus genomes, i.e., a library of improved complexity and diversity, than a library constructed in the absence of the inhibitor of poxvirus assembly, e.g., rifampicin. For example, the number of independent modified poxvirus genomes can be increased by at least about one-fold, about five-fold, about ten-fold, about fifteen-fold, about twenty-fold, about twenty-five-fold, or about thirty-fold or more as compared to a library constructed in the absence of the inhibitor of poxvirus assembly, e.g., rifampicin. Moreover, the methods of library construction provided herein can result in a library of increased virus titer than a library constructed in the absence of the inhibitor of poxvirus assembly. As shown in Example 1, for instance, 80 µg/ml of rifampicin is added 48 hours after transfection for a 48 hour treatment. Afterwards, the media is changed and cultured for another 48 hours. The end result is a yield that is at least live times greater than when rifampicin is not added.

According to the methods provided herein, an inhibitor of poxvirus assembly such as rifampicin can be used for any poxvirus, e.g., vaccinia virus library regardless of the starting plasmid and regardless of the type of protein of interest being screened in the library.

This disclosure employs, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of protein and antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in:

Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described can be followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds.) (1980) Selected Methods in Cellular Immunology (W.H. Freeman and Co., NY).

All of the references cited above, as well as all references cited herein, are incorporated herein by reference in their entireties. The following examples are offered by way of illustration and not by way of limitation.

EXAMPLES

Example 1: Vaccinia Library Construction Improvement with Rifampicin Treatment Library VHEH5VHA56RIresNeoFLVH3-30CR9B A Transfection was done with 36 μg of v7.5/tk viral DNA Cleaved with Not I and Apa I, 12 μg of transfer plasmid DNA, 54×10^6 plaque forming units (pfu) of fowlpox helper virus and 36×10^6 BSC-1 cells in 6 100 mm² plates. Five (5) plates of transfected cells were plated into 5 cell stackers 24 hours after transfection. 1 plate was seeded into a T175 flask. In order to determine the recombination efficiency, 2%, 1%, 0.5% and 0.25% of the transfected cells were seeded into 96-wells as count plates in duplicate. 48 hours after transfection, rifampicin was added at a concentration of 80 μg/ml to 1 set of count plates and to the T175 flask. The drug was maintained in the medium for 3 days. On Day 5, the medium was changed, and the cells were incubated for 2 more days without rifampicin. The stackers incubated without rifampicin were harvested on day 5.

The number of recombinant clones was calculated by Poisson distribution by observing by microscopy the percentage of wells that formed plaques in each 96 well plate.

The efficiency without Rifampicin was 23,652 clones/100 mm² plate.

The efficiency with Rifampicin was 113,148 clones/100 mm² plate, importantly, this was achieved using ⅛ of the number of cells and cell culture volume.

In follow-on experiments, the overall efficiency of clone production with rifampicin was approximately 10-fold higher than the efficiency without rifampicin.

What is claimed is:

1. A method of constructing a library comprising a plurality of polynucleotides of interest, comprising:
    (a) cleaving an isolated poxvirus genome to produce a first viral fragment and a second viral fragment, wherein the first fragment is nonhomologous with the second fragment;
    (b) providing a population of transfer plasmids each comprising a polynucleotide of interest flanked by a 5' flanking region and a 3' flanking region, wherein the 5' flanking region comprises a region homologous to the 3' end of the first viral fragment and the 3' flanking region comprises a region homologous to the 5' end of the second viral fragment; and wherein the transfer plasmids are capable of homologous recombination with the first and second viral fragments such that a viable poxvirus genome is formed;

(c) introducing the transfer plasmids and the first and second viral fragments into a mammalian host cell permissive for poxvirus infectivity;

(d) adding an inhibitor of poxvirus assembly; and (e) allowing the transfer plasmid and the first and second viral fragments to undergo homologous recombination, thereby producing a library of viable modified poxvirus genomes each comprising a heterologous nucleic acid.

2. The method of claim 1, further comprising (f) recovering the library.

3. The method of claim 1, wherein step (c) comprises transfecting the mammalian host cell with the transfer plasmids and the first and second viral fragments, and wherein the host cell is maintained in cell culture medium following transfection.

4. The method of claim 3, wherein the inhibitor of poxvirus assembly is rifampicin (rifampin) or a derivative thereof.

5. The method of claim 4, wherein the rifampicin or derivative thereof is added to the cell culture medium comprising the transfected cells at about 6 hours, about 12 hours, about 18 hours, about 24 hours, about 30 hours, about 36 hours, about 42 hours, about 48 hours, about 54 hours, or about 60 hours following transfection.

6. The method of claim 4, wherein the rifampicin or derivative thereof is added to the cell culture medium at a concentration of about 30 µg/ml, about 40 µg/ml, about 50 µg/ml, about 60 µg/ml, about 70 µg/ml, about 80 µg/ml, about 90 µg/ml, about 100 µg/ml, about 110 µg/ml, about 120 µg/ml, or about 130 µg/ml.

7. The method of claim 4, wherein the rifampicin or derivative thereof is allowed to remain cell culture medium for about one day, about two days, about three days, about four days or about five days.

8. The method of claim 7, wherein the cell culture medium is changed following treatment with rifampicin or a derivative thereof, and the transfected host cells further cultured without rifampicin for about one day, about two days, or about three days.

9. The method of claim 1, wherein the library comprises an increased number of independent modified poxvirus genomes than a library constructed in the absence of the inhibitor of poxvirus assembly.

10. The method of claim 9, wherein the number of independent modified poxvirus genomes is increased by at least about one-fold, about five-fold, about ten-fold, about fifteen-fold, about twenty-fold, about twenty-five-fold, or about thirty-fold as compared to a library constructed in the absence of the inhibitor of poxvirus assembly.

11. The method of claim 1, wherein the library comprises an increased virus titer than a library constructed in the absence of the inhibitor of poxvirus assembly.

12. The method of claim 1, wherein the isolated poxvirus genome comprises a first recognition site for a first restriction endonuclease and a second recognition site for a second restriction endonuclease; and wherein the first and second viral fragments are produced by digesting the viral genome with the first restriction endonuclease and the second restriction endonuclease, and isolating the first and second viral fragments.

13. The method of claim 1, wherein the isolated poxvirus genome is an isolated vaccinia virus genome.

14. The method of claim 13, wherein said isolated vaccinia virus genome is a WR genome, a Modified Vaccinia virus Ankara (MVA) genome, or a modified derivative thereof.

15. The method of claim 12, wherein the first and second restriction enzyme recognition sites are situated in a vaccinia virus HindIII J fragment.

16. The method of claim 13, wherein the first restriction enzyme is NotI.

17. The method of claim 13, wherein the second restriction enzyme site is ApaI.

18. The method of claim 13, wherein the isolated vaccinia virus genome is a v7.5/tk virus genome or a vEL/tk virus genome.

19. The method of claim 13, wherein the host cell is capable of packaging the modified vaccinia virus genomes into infectious vaccinia virus particles.

20. The method of claim 13, wherein the transfer plasmids and the first and second viral fragments are introduced into a mammalian host cell comprising a helper virus, wherein the host cell is non-permissive for the production of infectious virus particles of the helper virus, but supports packaging the modified vaccinia virus genomes into infectious vaccinia virus particles.

21. The method of claim 20, wherein the helper virus is a fowlpox virus.

22. The method of claim 13, wherein the 5' and 3' flanking regions of the transfer plasmid are capable of homologous recombination with a vaccinia virus thymidine kinase gene.

23. The method of claim 22, wherein the 5' and 3' flanking regions of the transfer plasmid are capable of homologous recombination with a vaccinia virus HindIII J fragment.

24. The method of claim 23, wherein the transfer plasmid comprises an insert nucleic acid ligated into a plasmid selected from the group consisting of:

(a) pVHE,
(b) pVLE,
(c) pVKE.

25. The method of claim 13, wherein the plurality of polynucleotides of interest each comprise a coding region of a polypeptide of interest capable of expression in a vaccinia virus-infected cell.

26. The method of claim 23, wherein the transfer plasmid further comprises a transcriptional control region in operable association with the polynucleotide of interest, and wherein the transcriptional control region functions in the cytoplasm of a vaccinia virus-infected cell.

27. The method of claim 26, wherein the transcriptional control region comprises a poxvirus promoter.

28. The method of claim 27, wherein the plurality of polynucleotides of interest each encode an antibody subunit polypeptide comprising an antibody heavy chain variable region or antigen-binding fragment thereof, an antibody light chain variable region or antigen-binding fragment thereof, or a combination thereof.

29. The method of claim 28, wherein the promoter is a vaccinia p7.5 promoter, a vaccinia pEL promoter, or a vaccinia MH-5 promoter.

30. The method of claim 28, wherein the antibody subunit polypeptide further comprises a constant region or fragment thereof, a signal peptide capable of directing cell surface expression or secretion of the antibody subunit polypeptide, or a combination thereof.

* * * * *

SEQUENCE LISTING

<160> NUMBER OF SEQ ID NOS: 3

<210> SEQ ID NO 1
<211> LENGTH: 1555
<212> TYPE: DNA
<213> ORGANISM: Artificial Sequence
<220> FEATURE:
<223> OTHER INFORMATION: Transfer Plasmid containing pVHE promoter

<400> SEQUENCE: 1

```
ggccaaaaat tgaaaaacta gatctattta ttgcacgcgg ccgcaaacca tgggatggag      60
ctgtatcatc ctcttcttgg tagcaacagc tacaggcgcg catatggtca ccgtctcctc     120
agggagtgca tccgccccaa cccttttccc cctcgtctcc tgtgagaatt ccccgtcgga     180
tacgagcagc gtggccgttg gctgcctcgc acaggacttc cttcccgact ccatcacttt     240
ctcctggaaa tacaagaaca actctgacat cagcagcacc cggggcttcc catcagtcct     300
gagagggggc aagtacgcag ccacctcaca ggtgctgctg ccttccaagg acgtcatgca     360
gggcacagac gaacacgtgg tgtgcaaagt ccagcacccc aacggcaaca agaaaagaa      420 cgtgcctctt ccagtgattg ctgagctgcc tcccaaagtg agcgtcttcg tcccaccccg     480
cgacggcttc ttcggcaacc cccgcagcaa gtccaagctc atctgccagg ccacgggttt     540 cagtcccgg cagattcagg tgtcctggct gcgcgagggg aagcaggtgg ggtctggcgt     600
caccacggac caggtgcagg ctgaggccaa agagtctggg cccacgacct acaaggtgac     660
tagcacactg accatcaaag agagcgactg gctcagccag agcatgttca cctgccgcgt     720
ggatcacagg ggcctgacct tccagcagaa tgcgtcctcc atgtgtgtcc ccgatcaaga     780
cacagccatc cgggtcttcg ccatcccccc atcctttgcc agcatcttcc tcaccaagtc     840
caccaagttg acctgcctgg tcacagacct gaccacctat gacagcgtca ccatctcctg     900
gacccgccag aatggcgaag ctgtgaaaac ccacaccaac atctccgaga gccaccccaa     960
tgccactttc agcgccgtgg gtgaggccag catctgcgag gatgactgga attccgggga    1020
gaggttcacg tgcaccgtga cccacacaga cctgccctcg ccactgaagc agaccatctc    1080
```

```
ccggcccaag ggggtggccc tgcacaggcc cgatgtctac ttgctgccac cagcccggga    1140
gcagctgaac ctgcgggagt cggccaccat cacgtgcctg gtgacgggct tctctcccgc    1200
ggacgtcttc gtgcagtgga tgcagagggg gcagcccttg tccccggaga agtatgtgac    1260
cagcgcccca atgcctgagc cccaggcccc aggccggtac ttcgcccaca gcatcctgac    1320
cgtgtccgaa gaggaatgga acacgggga gacctacacc tgcgtggtgg cccatgaggc    1380
cctgcccaac agggtcactg agaggaccgt ggacaagtcc accgaggggg aggtgagcgc    1440
cgacgaggag ggctttgaga acctgtgggc caccgcctcc accttcatcg tcctcttcct    1500
cctgagcctc ttctacagta ccaccgtcac cttgttcaag gtgaaatgag tcgac         1555

<210> SEQ ID NO 2
<211> LENGTH: 446
<212> TYPE: DNA
<213> ORGANISM: Artificial Sequence
<220> FEATURE:
<223> OTHER INFORMATION: Transfer plasmid containing pVKE promoter

<400> SEQUENCE: 2
ggccaaaaat tgaaaaacta gatctattta ttgcacgcgg ccgcccatgg gatggagctg      60
tatcatcctc ttcttggtag caacagctac acgggtgcac ttgactcgag atcaaacgaa    120
ctgtggctgc accatctgtc ttcatcttcc cgccatctga tgagcagttg aaatctggaa    180
ctgcctctgt tgtgtgcctg ctgaataact tctatcccag agaggccaaa gtacagtgga    240
aggtggataa cgccctccaa tcgggtaact cccaggagag tgtcacagag caggacagca    300
aggacagcac ctacagcctc agcagcaccc tgacgctgag caaagcagac tacgagaaac    360
acaaagtcta cgcctgcgaa gtcacccatc agggcctgag ctcgcccgtc acaaagagct    420
tcaacagggg agagtgttag gtcgac                                          446

<210> SEQ ID NO 3
<211> LENGTH: 455
<212> TYPE: DNA
<213> ORGANISM: Artificial Sequence
<220> FEATURE:
<223> OTHER INFORMATION: Transfer plasmid containing pVLE promoter

<400> SEQUENCE: 3
ggccaaaaat tgaaaaacta gatctattta ttgcacgcgg ccgcccatgg gatggagctg      60
tatcatcctc ttcttggtag caacagctac aggcgtgcac ttgactcgag aagcttaccg    120
tcctacgaac tgtggctgca ccatctgtct tcatcttccc gccatctgat gagcagttga    180
aatctggaac tgcctctgtt gtgtgcctgc tgaataactt ctatcccaga gaggccaaag    240
tacagtggaa ggtggataac gccctccaat cgggtaactc ccaggagagt gtcacagagc    300
aggacagcaa ggacagcacc tacagcctca gcagcaccct gacgctgagc aaagcagact    360
acgagaaaca caaagtctac gcctgcgaag tcacccatca gggcctgagc tcgcccgtca    420
caaagagctt caacagggga gagtgttagg tcgac                                455
```